(12) United States Patent
Baldwin

(10) Patent No.: US 10,371,370 B2
(45) Date of Patent: *Aug. 6, 2019

(54) ILLUMINATED PROTECTIVE COVERING FOR FOOT PEDALS

(71) Applicant: FACULTY PHYSICIANS AND SURGEONS OF LOMA LINDA UNIVERSITY SCHOOL OF MEDICINE, Loma Linda, CA (US)

(72) Inventor: Dalton Duane Baldwin, Loma Linda, CA (US)

(73) Assignee: FACULTY PHYSICIANS AND SURGEONS OF LOMA LINDA UNIVERSITY SCHOOL OF MEDICINE, Loma Linda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/048,260

(22) Filed: Jul. 28, 2018

(65) Prior Publication Data
US 2018/0356090 A1 Dec. 13, 2018

Related U.S. Application Data

(63) Continuation of application No. 15/592,907, filed on May 11, 2017, now Pat. No. 10,060,616, which is a
(Continued)

(51) Int. Cl.
*F21V 33/00* (2006.01)
*A61B 17/00* (2006.01)
(Continued)

(52) U.S. Cl.
CPC .......... *F21V 33/0068* (2013.01); *A61B 17/00* (2013.01); *A61B 46/10* (2016.02);
(Continued)

(58) Field of Classification Search
CPC . F21V 33/0068; A61B 46/10; F21W 2131/20; F21W 2131/202; F21W 2131/205; F21W 2131/208
See application file for complete search history.

(56) References Cited

U.S. PATENT DOCUMENTS 7,259,340 B2 8/2007 Blaha et al.
2003/0047434 A1 3/2003 Hanson et al.
(Continued)

FOREIGN PATENT DOCUMENTS

EP 1 958 568 8/2008

OTHER PUBLICATIONS

"Surgical Drape Footswitch Cover Non-Sterile Clear Plastic 17"x15"—100 Per Case", PDC Healthcare, http://www.pdchealthcare.com/footswitch-cover-17-wx15-d-100-cs-fsc1715.html, Oct. 18, 2014 (retrieved on Jan. 12, 2016).
(Continued)

*Primary Examiner* — Robert J May
(74) *Attorney, Agent, or Firm* — Womble Bond Dickinson (US) LLP

(57) ABSTRACT

A system and method of illuminating a foot pedal with an illuminated protective covering. The illuminated protective covering can include a plurality of illuminating devices surrounding at least a majority of a perimeter of the foot pedal. The illuminated protective covering can also include a sheet surrounding the upper surface and the lower surface of the foot pedal and the plurality of illuminating devices, the sheet being configured to protect the foot pedal from debris during use. A friction portion can be attached to the sheet, the friction portion being positioned on the sheet such that the friction portion is adjacent the bottom surface of the foot pedal when the sheet surrounds the foot pedal, the friction portion being configured to prevent sliding of the foot pedal against the floor or other surface.

15 Claims, 15 Drawing Sheets

Related U.S. Application Data continuation-in-part of application No. PCT/US2015/061523, filed on Nov. 19, 2015.

(60) Provisional application No. 62/083,098, filed on Nov. 21, 2014, provisional application No. 62/338,403, filed on May 18, 2016.

(51) Int. Cl.
| | |
|---|---|
| *G05G 1/30* | (2008.04) |
| *A61B 46/10* | (2016.01) |
| *A61B 90/30* | (2016.01) |
| *A61B 90/92* | (2016.01) |
| *F21V 3/04* | (2018.01) |
| *F21V 23/04* | (2006.01) |
| *F21V 31/00* | (2006.01) |
| *G05G 1/44* | (2008.04) |
| *G05G 25/04* | (2006.01) |
| *H01H 3/14* | (2006.01) |
| *H01H 9/04* | (2006.01) |
| *H01H 9/18* | (2006.01) |
| *A61B 18/00* | (2006.01) |
| *F21W 131/20* | (2006.01) |

(52) U.S. Cl.
CPC .............. *A61B 90/30* (2016.02); *A61B 90/92* (2016.02); *F21V 3/04* (2013.01); *F21V 23/04* (2013.01); *F21V 31/00* (2013.01); *G05G 1/30* (2013.01); *G05G 1/44* (2013.01); *G05G 25/04* (2013.01); *A61B 18/00* (2013.01); *A61B 2017/00876* (2013.01); *A61B 2017/00907* (2013.01); *A61B 2017/00951* (2013.01); *A61B 2017/00973* (2013.01); *A61B 2090/309* (2016.02); *F21W 2131/20* (2013.01); *H01H 3/14* (2013.01); *H01H 9/04* (2013.01); *H01H 9/18* (2013.01)

(56) References Cited

U.S. PATENT DOCUMENTS

| | | |
|---|---|---|
| 2006/0090990 A1 | 5/2006 | Blaha et al. |
| 2010/0198200 A1 | 8/2010 | Horvath |

OTHER PUBLICATIONS

"Martelli Non Slip Sewing Machine Foot Pedal Pad", Amazon.com, Inc., https://www.amazon.com/Martelli-Slip-Sewing-Machine-Pedal/dp/B004309DM4, Jul. 1, 2013 (retrieved on Jan. 12, 2016).

International Search Report and Written Opinion issued in corresponding International Application No. PCT/US2015/061523 dated Feb. 2, 2016.

Extended European Search Report issued in corresponding European Application No. 15860535.2 dated Sep. 3, 2018.

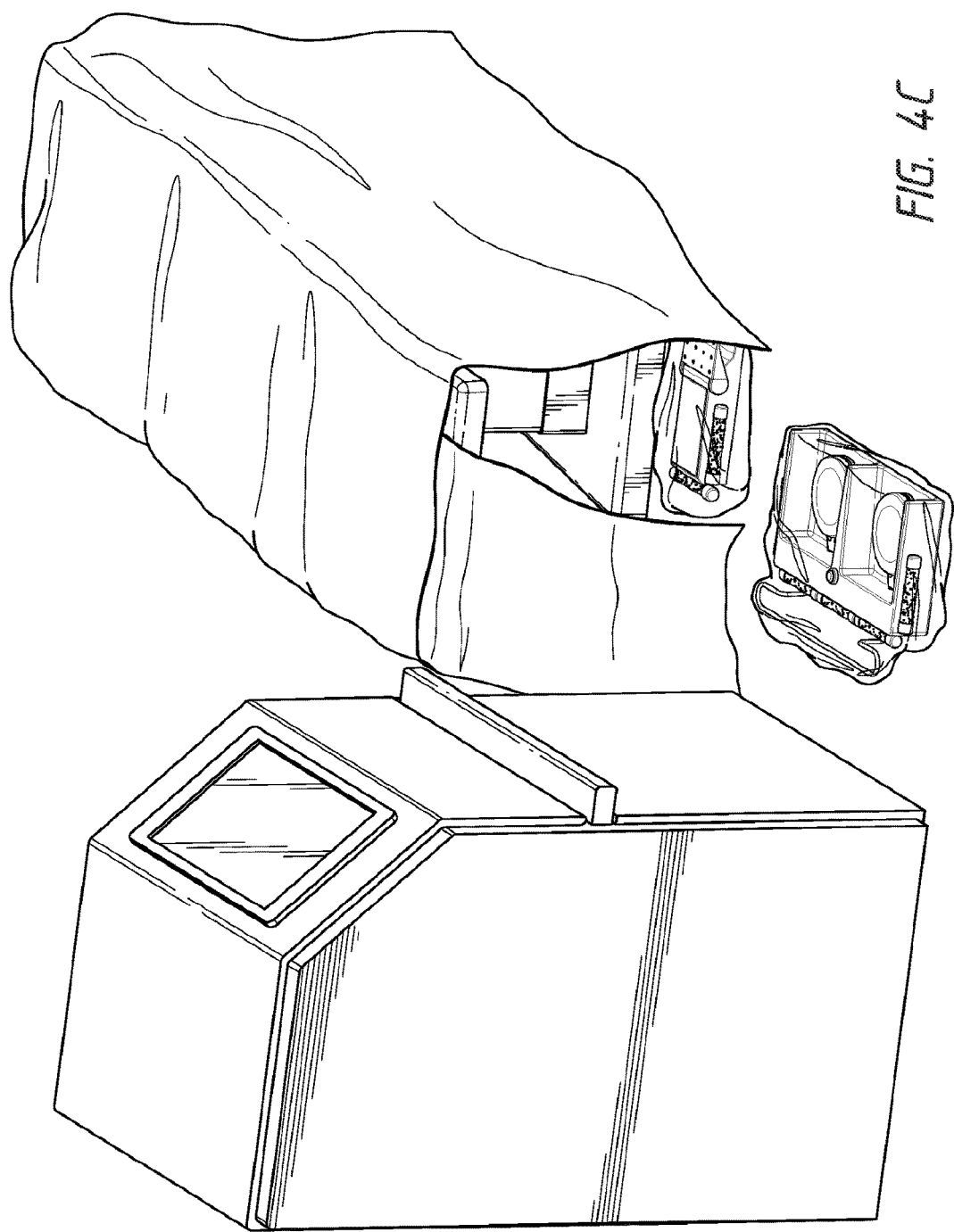

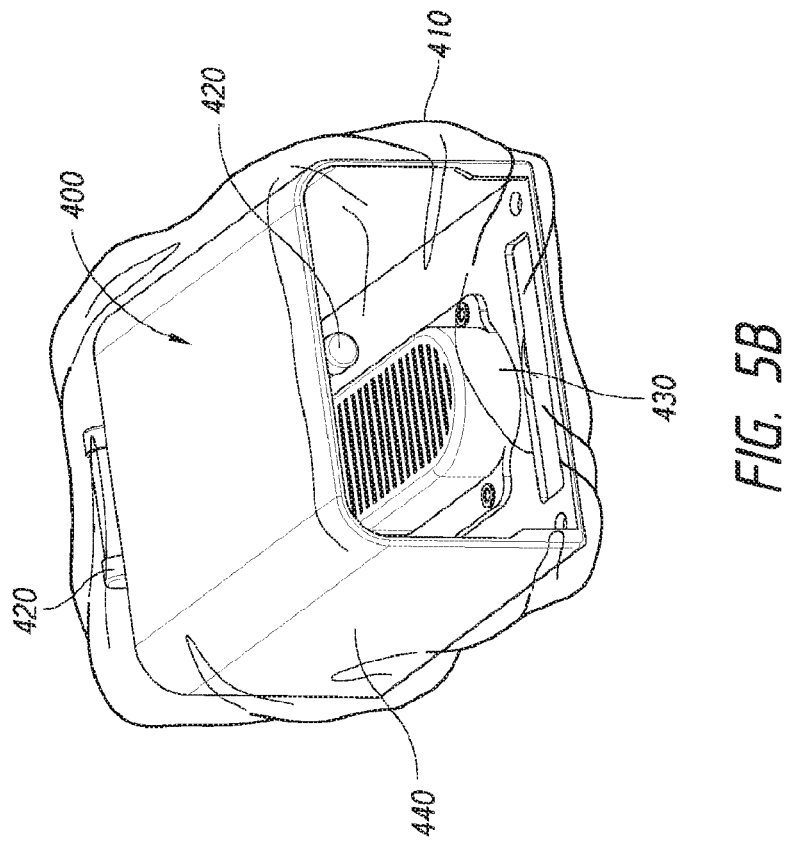
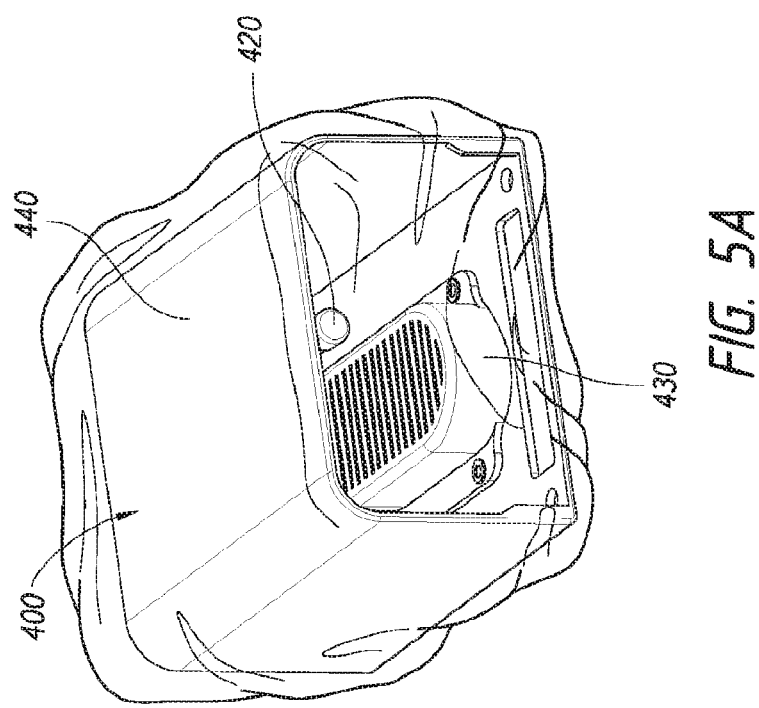

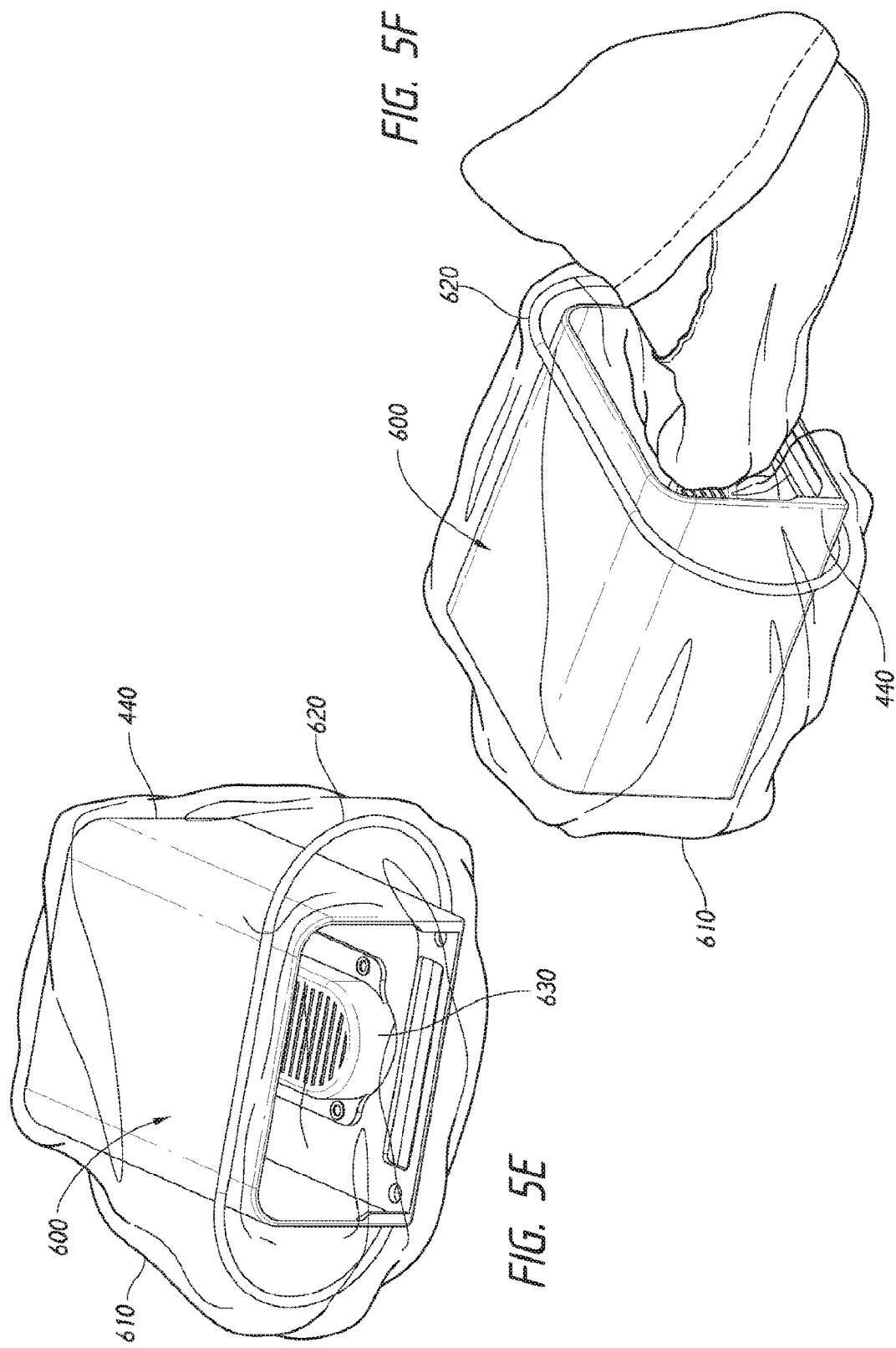

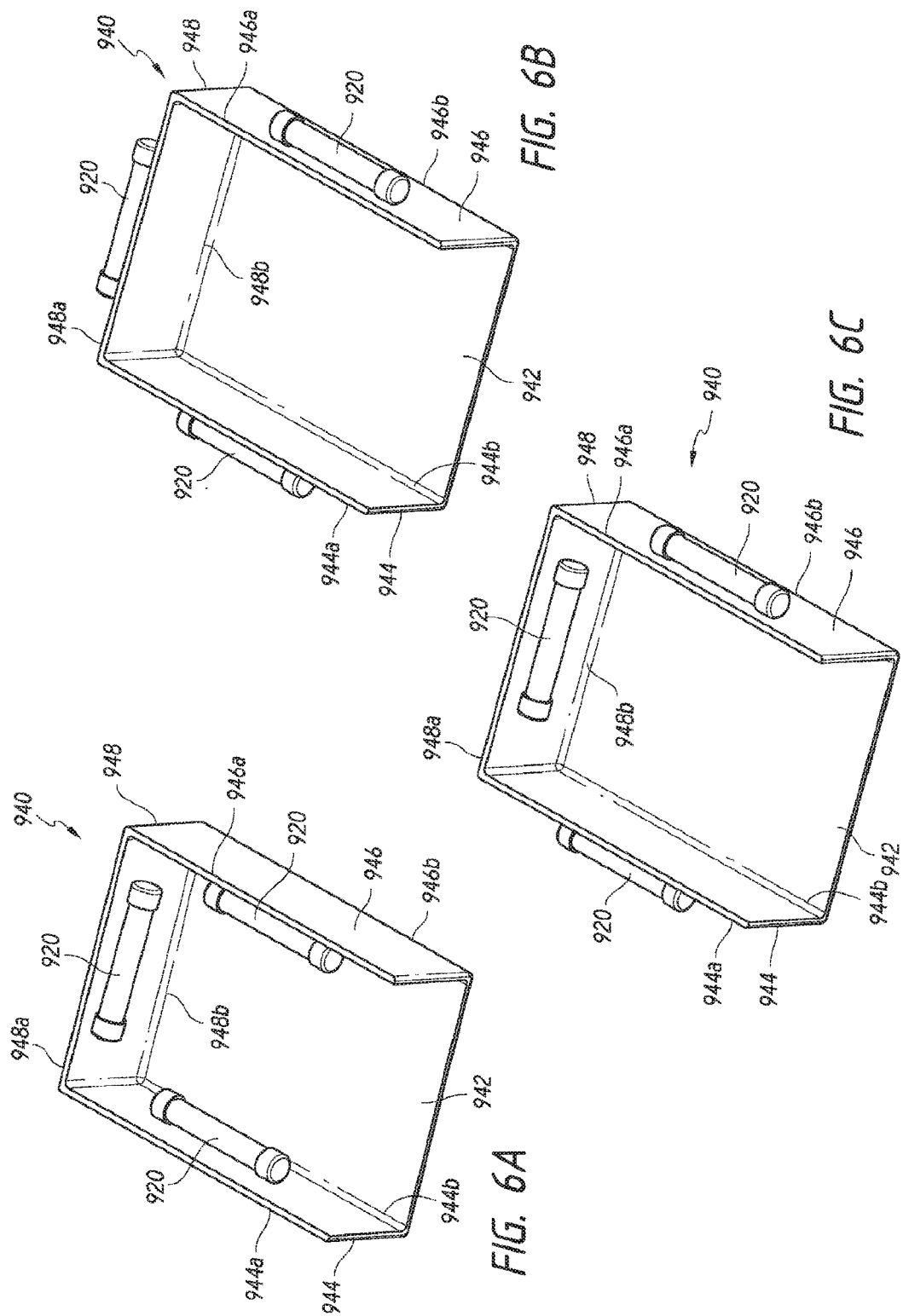

ILLUMINATED PROTECTIVE COVERING FOR FOOT PEDALS

INCORPORATION BY REFERENCE TO ANY PRIORITY APPLICATIONS

The present application is a Continuation of U.S. Non-Provisional application Ser. No. 15/592,907, titled "ILLUMINATED PROTECTIVE COVERING FOR FOOT PEDALS," filed May 11, 2017, which is a Continuation in Part of International Application No. PCT/US2015/061523, titled "ILLUMINATED PROTECTIVE COVERING," filed Nov. 19, 2015, which claims priority to and the benefit of U.S. Provisional Application No. 62/083,098, titled "FOOT PEDAL LIGHTS," filed Nov. 21, 2014, the full disclosure of which is incorporated herein by reference. This application also claims priority to and the benefit of U.S. Provisional Application No. 62/338,403, titled "ILLUMINATED PROTECTIVE COVERING," filed May 18, 2016, the full disclosure of which is incorporated herein by reference.

BACKGROUND

Field

The present disclosure relates to illuminated protective coverings and associated methods that can be used with surgical devices.

Description of the Related Art

Foot pedals are used in a variety of environments, including surgical environments. Surgical devices are used in an operating room during surgical procedures. The surgical devices can include foot pedals that are frequently placed on the floor beneath the patient and can be depressed to activate and operate the surgical device.

SUMMARY

Certain aspects of the present disclosure are directed toward an illuminated protective covering for a surgical device, for example a foot-activated surgical device that can be used in an operating room during surgery, and associated methods.

Foot pedals can be used in many different applications and are frequently used to operate devices and/or machinery. In some implementations, the foot pedals can be used for playing musical instruments (such as pianos, keyboards, drums, and guitars). In some implementations, the foot pedals can be used with sound equipment, e.g., to control amplifiers, synthesizers, laptops, etc., in sound booths, DJ booths, or other similar environments. In some implementations, the pedals can be used with movie equipment, e.g., to control sound equipment or lighting equipment. In some implementations, the pedals can be used for the operation of motor vehicles. In some implementations, the foot pedals can be used with portable devices such as sewing machines. In some implementations, the foot pedals described herein can be used during medical procedures, such as with surgical foot pedals. Each of these pedals can be placed on the floor near the foot of the user.

During a surgical procedure, a surgeon can have different types of foot pedals to operate one of the many pieces of equipment during surgery. As an example, in urology, a first foot pedal can be used to operate a laser to break stones and treat tumors, a second foot pedal can be used to perform electrocautery to trim out prostate and bladder tumors, a third foot pedal can be used to operate a C-arm, and a fourth foot pedal can be used to operate an ultrasonic lithotripsy device. Each of these pedals can be placed on the floor beneath the patient on the operating table.

Furthermore, many surgical procedures, such as those involving endoscopy, laparoscopy, and robotic devices, as well as other, non-surgical uses of foot pedals, can require a darkened environment or areas with low light.

The darkened environment and the location of the foot pedals creates a situation that can result in human error as the inability to easily and properly locate the proper foot pedal can cause the wrong pedal to be depressed and the wrong device to be activated. In surgical contexts, operating the wrong foot pedal can result in significant patient and surgeon harm. As well, the darkened environment can cause the user to have difficulty locating the foot pedal, which can lead to missing or kicking of the foot pedal.

To reduce surgeon or other user error, the foot pedal can be provided with an illuminated protective cover that allows the surgeon or other user to easily identify the appropriate foot pedal to be used. The illuminated protective cover can also protect the foot pedal from moisture damage as well as debris generated from the environment, such as during a surgical procedure. In some examples, the foot pedal can be color coded to help the surgeon or other user identify the purpose of each pedal as well as the proper placement of the foot. In some examples, a foot pedal can have a number of different actuators (e.g., pedals, buttons, etc.). The illuminated protective cover can help the surgeon or other user identify the location of each of the different actuators.

The illumination devices and protective cover can be separately attached such that the surgeon can easily adapt the illuminated protective cover for any device being used with a foot pedal. Further, the illumination devices and/or the protective cover can be disposable and configured to be used on a foot pedal of any size or shape. Disposability is important for maintaining a clean surgical environment.

In some examples, the illuminated protective cover can further include a frame to provide additional protection to the foot pedal and for elevated lighting of the foot pedal. The illuminated protective cover can also include an attachable friction surface to prevent the covered foot pedal from slipping against a surface.

Accordingly, the present disclosure is directed to a system for illuminating one or more foot pedals, according to an embodiment. In an embodiment, the system can include one or more foot pedals, each of the foot pedals: being configured to transition from an initial position to a depressed position; being positioned to activate a function of the foot pedal when in the depressed position; and having an upper surface and a lower surface, the lower surface being adapted to be positioned on a floor or other surface.

In an embodiment, the system can further include a plurality of illuminating devices surrounding a majority of a perimeter of each of the one or more foot pedals to illuminate light therefrom.

In an embodiment, the system can further include a sheet connected to each of the one or more foot pedals and substantially covering the upper surface and the lower surface of each of the one or more foot pedals and the plurality of illuminating devices, the sheet being positioned to protect each of the one or more foot pedals from debris, the sheet having an optically transmissive material such that light when illuminating from the plurality of illuminating devices is visible external to the sheet, the optically transmissive material being sufficiently flexible to substantially conform to a shape of each of the one or more foot pedals.

In an embodiment, the system can include a friction portion attached to the sheet, the friction portion being positioned on the on the sheet such that the friction portion is adjacent the bottom surface of each of the one or more foot pedals when the sheet covers each of the one or more foot pedals, the friction portion being positioned to prevent sliding of each of the one or more foot pedals against the floor or other surface.

In an embodiment, the system can include a frame positioned to receive the one or more foot pedal.

In an embodiment, the frame can have a bottom wall; first and second walls extending upward from opposite lateral sides of the bottom wall; and a third wall extending between the first and second walls and along a side of the bottom wall.

In an embodiment, the sheet can be further connected to the frame.

In an embodiment, each of the plurality of illuminating devices can be positioned on one or more of an inside surface of the frame and an outside surface of the frame.

In an embodiment, the system can include a switch for activating and deactivating the plurality of illuminating devices.

In an embodiment, each of the plurality of illuminating devices can be removably attached to one or more of the one or more foot pedal and the sheet.

In an embodiment, each of the plurality of illuminating devices can be located at a height above a top surface of each of the one or more foot pedals.

The present disclosure is also directed to an illuminated protective covering to cover and illuminate one or more foot pedals, according to an embodiment. In an embodiment, the covering can include a frame positioned to receive the one or more foot pedals, the frame including a bottom wall; first and second walls extending upward from opposite lateral sides of the bottom wall; and a third wall extending between the first and second walls and along a side of the bottom wall.

In an embodiment, the covering can include a plurality of illuminating devices to illuminate light therefrom, one or more of the plurality of illuminating devices being attached to each of the first, second, and third walls of the frame.

In an embodiment, the covering can include a sheet positioned to cover the frame and the plurality of illuminating devices to provide protection from debris, the sheet having an optically transmissive material such that light when illuminating from the plurality of illuminating devices is visible external to the sheet, the optically transmissive material being sufficiently flexible to substantially conform to the one or more foot pedals; and a friction portion positioned on the sheet such that the friction portion is adjacent a bottom surface of each of the one or more foot pedals when the sheet is positioned on the one or more foot pedals, the friction portion positioned to prevent sliding of the one or more foot pedals against a floor or other surface.

The present disclosure is further directed to a method for illuminating one or more foot pedals, according to an embodiment. In an embodiment, the method can include attaching an illuminated covering to the one or more foot pedals.

In an embodiment, the covering can include a plurality of illuminating devices. In an embodiment, the plurality of illuminating devices can surround a majority of a perimeter of the one or more foot pedals when attached to the one or more foot pedals.

In an embodiment, the covering can include a sheet. In an embodiment, the sheet can have an optically transmissive material such that light when illuminating from the plurality of illuminating devices is visible external to the sheet, the optically transmissive material being sufficiently flexible to substantially conform to a shape of the one or more foot pedals; and a friction surface positioned to prevent the one or more foot pedals from slipping against a floor or other surface, the friction surface being adjacent to a lower surface of the one or more foot pedals when the sheet is covering the one or more foot pedals.

In an embodiment, the method can include covering upper and lower surfaces of the one or more foot pedals and the plurality of illuminating devices with the sheet, the sheet being positioned to protect the one or more foot pedals from moisture and other debris.

In an embodiment, the method can include securing the illuminated covering to the one or more foot pedals.

In an embodiment, the method can include removing the illuminated covering after use of the one or more foot pedals.

Other aspects and features of the present disclosure will become apparent to those of ordinary skill in the art after reading the detailed description herein and the accompanying figures.

BRIEF DESCRIPTION OF DRAWINGS

Various embodiments are depicted in the accompanying drawings for illustrative purposes, and should not be interpreted as limiting the scope of the embodiments. Furthermore, various features of different disclosed embodiments can be combined to form additional embodiments, which are part of this disclosure:

FIGS. 4A-4C illustrate the illuminated protective coverings of FIGS. 1A-B, 2A-B, and 3A-B activated in a darkened environment.

FIGS. 5A-5H illustrate an embodiment of a protective frame that can be used with an illuminated protective covering, wherein the protective frame is disposed about a foot-activated device and the illuminating device can be located in a number of different locations.

FIGS. 6A-6C illustrate another embodiment of the protective frame with a plurality of illuminating devices attached.

DETAILED DESCRIPTION

Figure 1A:
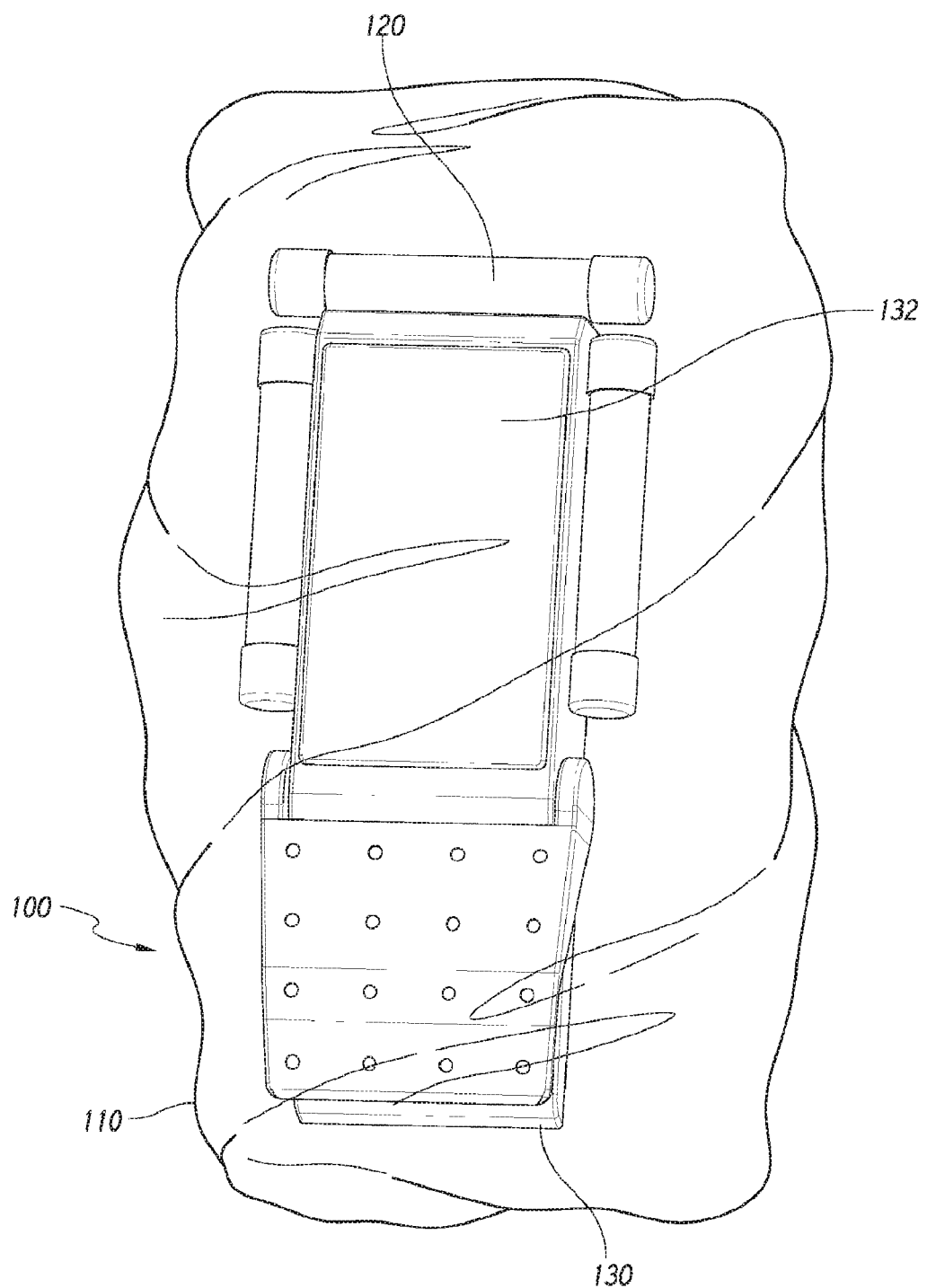
FIGS. 1A-1B illustrate an embodiment of an illuminated protective covering for a foot-activated device with a single foot pedal.

Various illuminated device covers, assemblies, and methods are disclosed to illustrate various examples that may be employed to achieve one or more desired improvements. For purposes of presentation, certain embodiments are disclosed with respect to a surgical device with a foot pedal, but the disclosed invention can be used in other contexts as well. Indeed, the described embodiments are examples only and are not intended to restrict the general disclosure presented and the various aspects and features of this disclosure. The general principles described herein may be applied to embodiments and applications other than those discussed herein without departing from the spirit and scope of the disclosure. This disclosure should be accorded the widest scope consistent with the principles and features that are disclosed or suggested herein.

Although certain aspects, advantages, and features are described herein, it is not necessary that any particular embodiment include or achieve any or all of those aspects, advantages, and features. For example, some embodiments may not achieve the advantages described herein, but may achieve other advantages instead. No feature, component, or step is necessary or critical.

Overview

The present disclosure is directed toward an illuminated protective cover that can be used in connection with a foot pedal of a foot-activated device, and in an embodiment can be placed over a surgical foot pedal. As described below, the protective cover can include a support structure (e.g., a frame or sheet of material) and at least one illuminating device. For example, a protective sheet can be secured around the foot pedal to protect the foot pedal from damage from moisture or other debris generated from the environment, such as from a surgical procedure in an embodiment (see, e.g., FIGS. 1A-1B, 2A-2B, 3A-3B, 4A-4B, and 5A-5H). Further, the protective sheet can be optically transmissive to allow the foot pedal to be easily visible. In an embodiment, the foot pedal can be positioned within a frame that supports the at least one illuminating device (see, e.g., FIGS. 6A-6C).

The illuminated protective cover can include one or more illuminating devices that enable a user, such as a surgeon, to easily identify and access the appropriate foot pedal, for example during surgery. In some configurations, the illuminated protective cover and/or the one or more illuminating devices can be customized for foot pedals having specific sizes, such as specific surgical foot pedal devices. In other configurations, there may be a "one-size fits all" kit where the illuminated protective cover and the illuminating device(s) can be used for any number of different foot pedal designs. In either configuration, the plurality of illuminated devices may be removably or permanently attached to the foot pedal and/or the protective sheet. As described further below, the system may include a separate frame structure for receiving the surgical foot pedal, which may be attached to or retain one or more illuminating devices. The frame can be configured to provide the foot pedal with additional protection or to allow the placement of the illuminating devices at additional elevations and/or angles.

Although the following description of the illuminated protective cover will be discussed in relation to a foot pedal, the present disclosure is not intended to be limiting to foot pedals. The described illuminated protective cover can be used with any number of compressible devices (e.g., foot switches, foot buttons, etc.) that are used frequently and need to be protected from the environment, for example for use in surgical operating rooms.

Protective Cover and Illuminating Device(s)

Figure 1B:
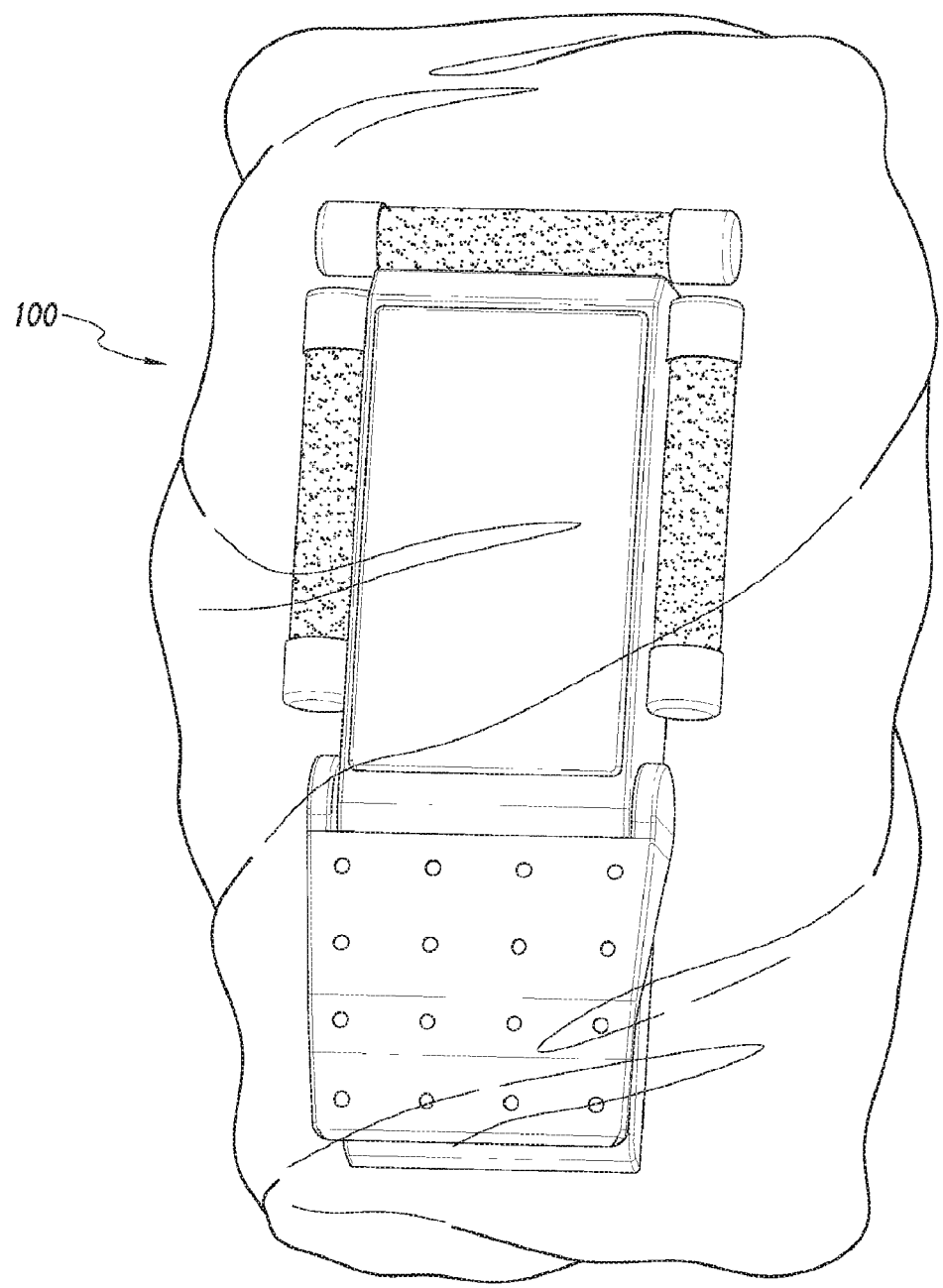
Figure 2A:
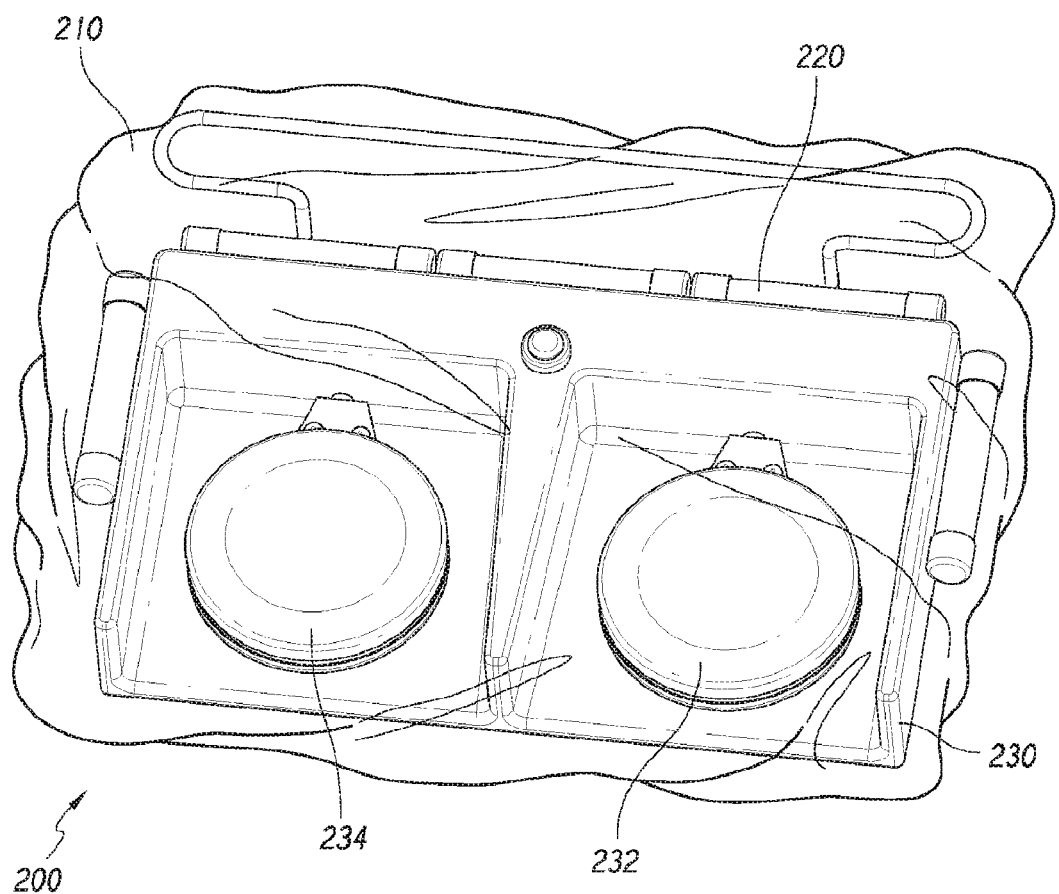
FIGS. 2A-2B illustrate an embodiment of an illuminated protective covering for a foot-activated device with two foot pedals.
Figure 2B:
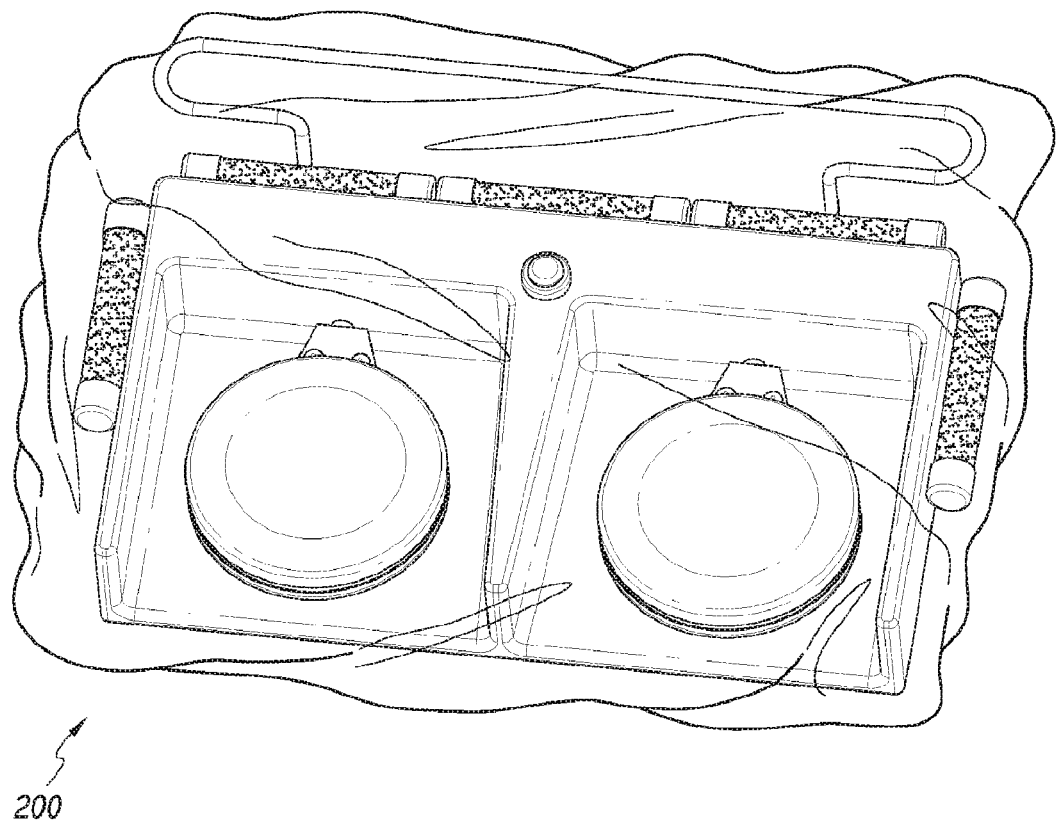

FIGS. 1A-1B, 2A-2B, and 3A-3B illustrate embodiments of the illuminated protective cover covering various examples of foot pedals. As will be described in more detail below, the illuminated protective cover can include a protective sheet and a plurality of illuminating devices. The protective sheet can be transparent or translucent such that the illuminating device can brighten the foot pedal such that the user can visibly see the location of the foot pedal through the protective sheet. As seen in FIGS. 1B, 2B, and 2C, the brightness of the illuminating device allows the location of the foot pedal to be visible even in dim lighting.

FIG. 1A illustrates an illuminated protective cover 100 disposed about a device 130 with a first pedal 132. In an embodiment, device 130 can be an example of a surgical device. As noted above, the illuminated protective cover 100 can include a protective sheet 110 and a plurality of illuminating devices 120 placed around the foot pedal 132 of the surgical device 130.

The protective sheet 110 can be in the form of a flat sheet or a bag. As described above, in some configurations, the protective sheet 110 can be customized for specific foot pedal designs. In other configurations, the protective sheet 110 can be sufficiently large to fit any sized device 130 and can be configured to allow a user to resize the protective sheet 110 as appropriate. For example, the protective sheet 110 can have a size of 20 inches by 20 inches. The protective sheet 110 can be wrapped or secured about the device 130 such that the protective sheet 110 folds or conforms to the surface of the foot pedal 132 of the device 130. The protective sheet 110 provides a protective covering about the surgical device 130 but does not interfere with the function of the foot pedal 132 of the device 130.

The protective sheet 110 can be secured about the surface of the device 130 to protect the device 130 from moisture and other debris generated from the environment; for example, during the surgical procedure. For example, the protective sheet 110 can be secured by tying and/or knotting the ends of the protective sheet 110 about the device 130. Additionally or alternatively, the protective sheet 110 can be secured using adhesive, string, a wire, an elastic band, etc.

The protective sheet 110 can be made from a transparent or translucent material that allows the device 130 and the foot pedal 132 to be visible. The protective sheet 110 can be made of plastic. As well, the protective sheet 110 can be disposable and easily discarded after each use. A disposable protective sheet 110 can allow the disposable protective sheet 110 to be cheaply purchased by the user. As well, the disposable and customizable configuration of the protective sheet 110 can also reduce costs as the same disposable protective sheet 110 can be adapted to a device, such as a surgical instrument, of any shape or size.

The illuminated protective cover 100 can include one or more illuminating devices 120 that light up the device 130 and location of the foot pedal 132. The illuminating device 120 is attached to at least one side adjacent to the foot pedal 132 of the device 130. As illustrated in FIG. 1A, each of the plurality of surgical devices 130 can be attached such that an illuminating device 120 is placed on the surface of one end of the device 130, on the left of the device 130, and on the right of the device 130. This can allow the user to locate the position of the foot pedal 132 based on the illuminating device 120.

The height of the placement of each of the illuminating devices 120 can also be varied to allow the user to locate the foot pedal 132 and better adjust the position of the user's foot. The illuminating devices 120 can be placed at a number of heights such as the base of the device 130, between the base and the top surface of the device 130, or above the top surface of the device 130.

The plurality of illuminating devices 120 can be removably or permanently secured in a number of ways. In some examples, the plurality of illuminating devices 120 can be attached directly to the device 130. In some embodiments, the plurality of illuminating devices 120 can be secured to the inside or outside surface of the protective sheet 110.

The plurality of illuminating devices 120 can be secured in a number of ways such as through using an adhesive or attaching each of the illuminating devices 120 with a separate component (e.g., a magnet, a clip, a wire, or otherwise) that can be configured to engage with the device 130 or the protective sheet 110. In other examples, the protective sheet 110 may include one or more pockets or other features to retain the illuminating devices 120.

The illuminating devices 120 can come in a variety of shapes and sizes. In some embodiments, the illuminating device 120 is tubular. The illuminating devices 120 can be rigid and any length. For example, the illuminating devices 120 can be attached end-to-end such that the illuminating devices 120 can span the entire length of a side of the device or only a portion (e.g., substantially the entire length of a side of the device 130, a majority of the entire length of a side of the device 130, about half of the entire length of a side of the device 130, less than half of the entire length of a side of the device 130, or intermittently along the side of the device 130). The illuminating device 120 can also be bendable and/or malleable. For example, a single illuminating device 120 can be bent to wrap around portions of the device 130.

The illuminating device 120 can be disposable such that it provides a one-time activation. For example, the structure can make light through chemiluminescence, with the outer covering being rigid or flexible. In some examples, the illuminating device 120 is a glow stick. A disposable illuminating device 120 can allow the disposable illuminating device 120 to be cheaply purchased by the user. As well, the disposable and customizable nature of the plurality of disposable illuminating devices 120 can also reduce costs as the same disposable illuminating devices 120 can be attached to a surgical device of any shape or size.

The illuminating device 120 can also be non-disposable. For example, each illuminating device 120 can be composed of one or more LEDs. The illuminating device 120 can be battery powered or require an electrical outlet to provide power. The illuminating device 120 can include an on and off switch to activate the illuminating device 120.

The illuminating device 120 can be configured to emit a red light. Red lights have lower wavelengths and can be less disruptive to the eye in a darkened environment. In other examples, the illuminating device 120 can come in any variety of colors such as red, blue, green, yellow, purple, orange, pink, etc. When a plurality of devices or foot pedals are being used, the multiple colors of illuminating devices 120 can be used to help the user identify the purpose of each of the illuminating devices 120.

Figure 3A:
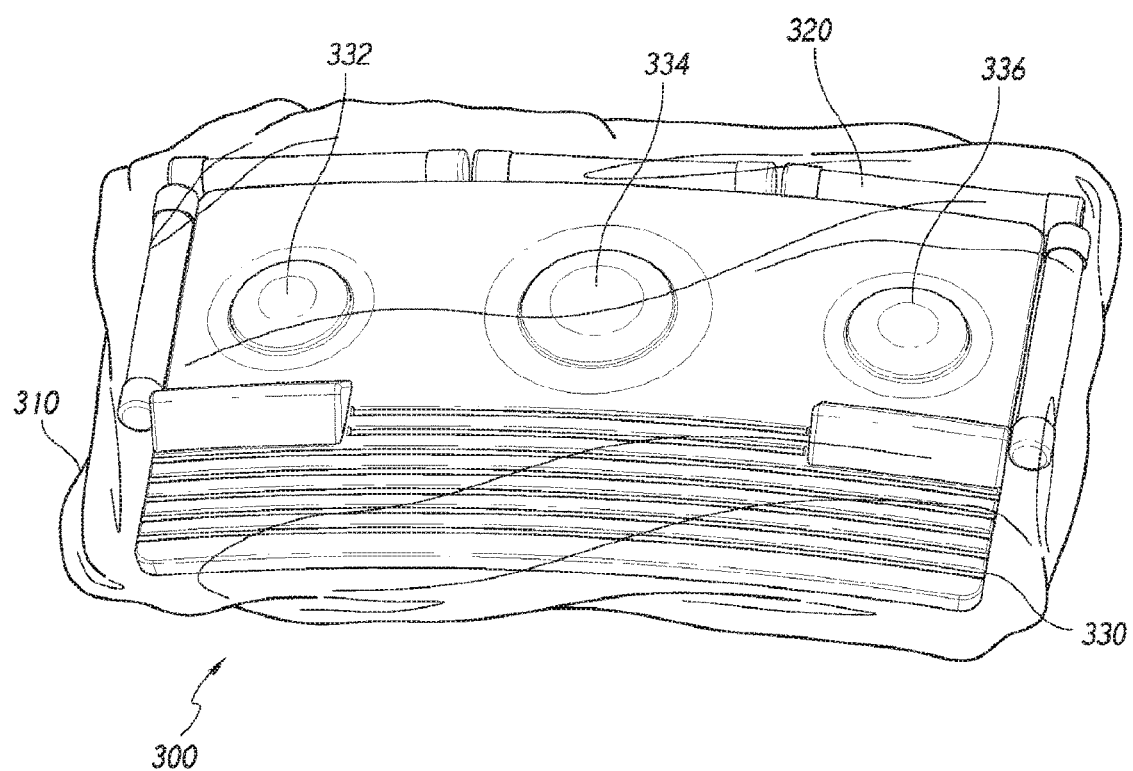
FIGS. 3A-3B illustrate an embodiment of an illuminated protective covering for a foot-activated device with three foot pedals.

FIGS. 2A and 3A illustrate illuminated protective covers 200, 300 disposed about devices 230, 330 that include a plurality of foot pedals. In an embodiment, devices 230, 330 can be examples of surgical devices. The illuminated protective covers 200, 300 resemble or are identical to the system 100 in many respects. Accordingly, numerals used to identify components of the illuminated protective covers 200, 300 are incremented by a factor of one hundred to identify like features of the illuminated protective covers 200, 300. This numbering convention generally applies to the remainder of the figures. Any component or step disclosed in any embodiment in this specification can be used in other embodiments.

The illuminated protective cover 200, like the illuminated protective cover 100, includes a protective sheet 210 and a plurality of illuminating devices 220. The illuminated protective cover 200 is disposed about the device 230 that includes a foot pedal 232 and a foot pedal 234. Each of a plurality of illuminating devices 220 is attached around the device 230 to frame the borders of the device 230. As shown in FIG. 2B, the placement of the plurality of illuminating devices 220 can allow the user to see the location of the foot pedal 232 and foot pedal 234 on the surgical device 230.

The placement of the illuminating device 220 can also provide the user with a frame of reference of where the foot should be placed to engage either of the foot pedals. For example, the user can use the location of the plurality of illuminating devices 220 to know that by placing his foot closer to the right-most illuminating device 220, he will activate the foot pedal 232 located on the right. Similarly, the user will know that by placing his foot closer to the left-most illuminating device 220, he will activate the foot pedal 234 located on the left. The illuminating devices 220 can also be placed between each of the foot pedals 232, 234 such that the user can easily identify the location of each of the foot pedals 232, 234.

Similarly, FIG. 3A illustrates an example of how the illuminated protective cover 300 can allow the user to identify and easily locate a surgical device 330 with a plurality of pedals. The illuminated protective cover 300 includes a protective sheet 310 and a plurality of illuminating devices 320 disposed about the surgical device 330. Because of the number of foot pedals on the device 330, the device 330 is wider than the devices illustrated in FIGS. 1A and 2A. To frame the device 330, the illuminated protective cover 300 can include additional illuminating devices 320 to frame/line the front end of the device 330. In some examples, a plurality of illuminating devices 320 can be attached to the device 330 such that the plurality of illuminating devices 320 line up end-to-end. In the device 330 illustrated in FIG. 3A, the device 330 includes a foot pedal 332, a foot pedal 334, and a foot pedal 336.

Figure 3B:
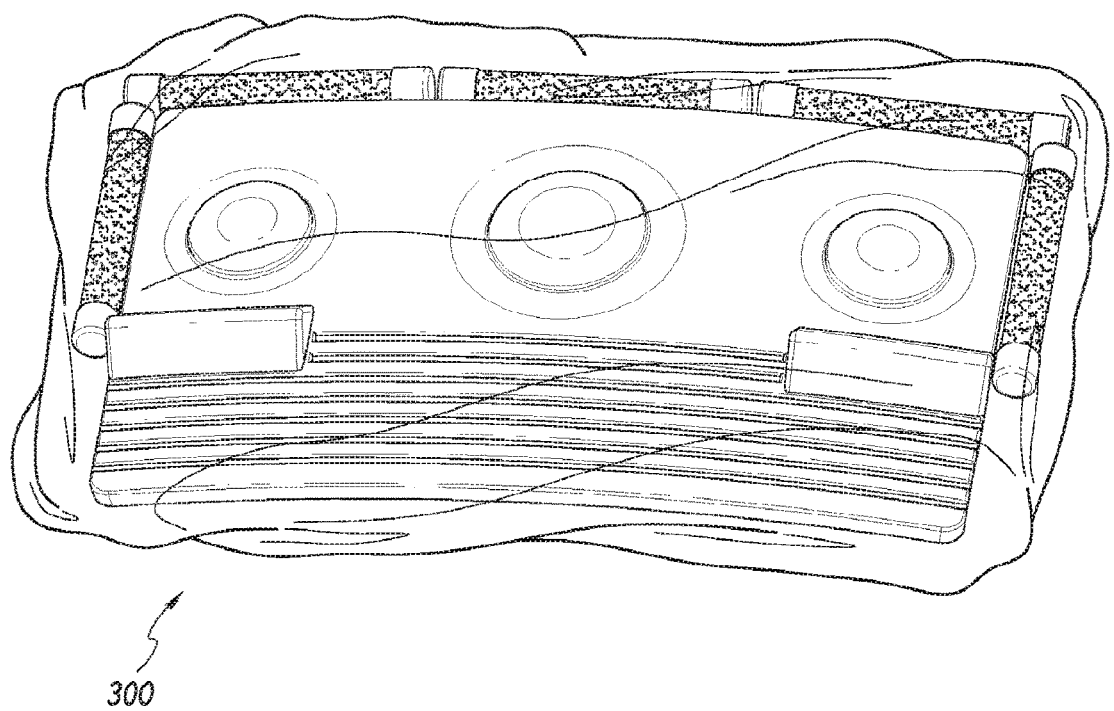

As with FIG. 2B, FIG. 3B illustrates the illuminated protective cover 300 illuminating the device 330 in a darkened environment. In some examples, because of the placement of the plurality of illuminating devices 320, the user will be able to locate the foot pedal 332 near the left-most illuminating device 320, the foot pedal 336 near the right-most illuminating device 320, and the foot pedal 334 by placing his foot in the middle of the device 330 framed by the plurality of illuminating devices 320. The illuminating devices 320 can also be placed between each of the foot pedals 332, 334, 336 such that the user can easily identify the location of each of the foot pedals 332, 334, 336.

The illuminated protective cover can be configured to accommodate a surgical device with any number of foot pedals. By using the plurality of illuminating devices to frame the outside surface of the device, the illuminating devices can allow the user to see the foot pedals, or to provide the user with a frame of reference as to where he is placing his foot. As well, as described above, an illuminating device can be placed between each of the foot pedals to help the user more precisely locate each of the foot pedals on the device.

Figure 4A:
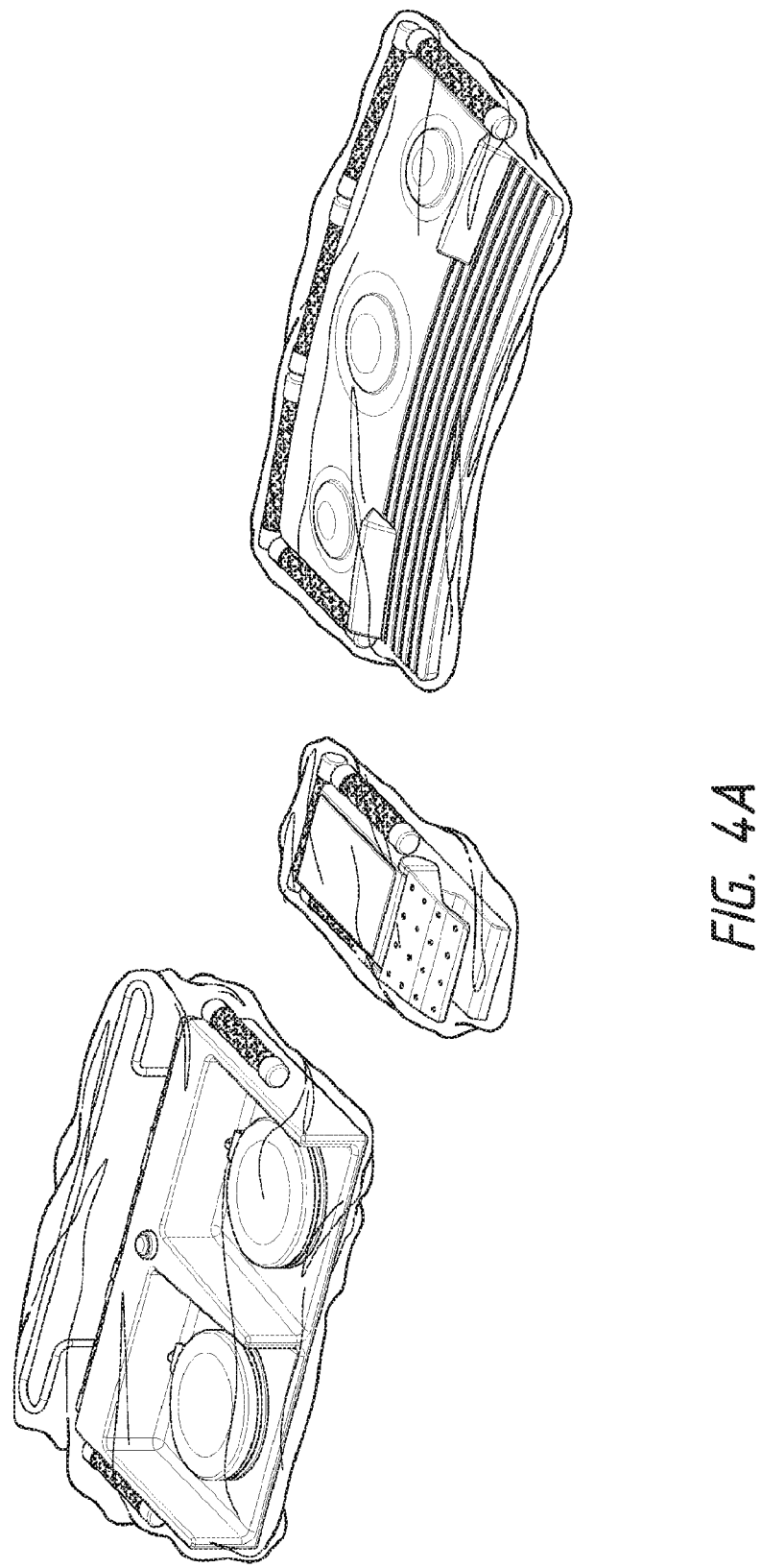
Figure 4B:
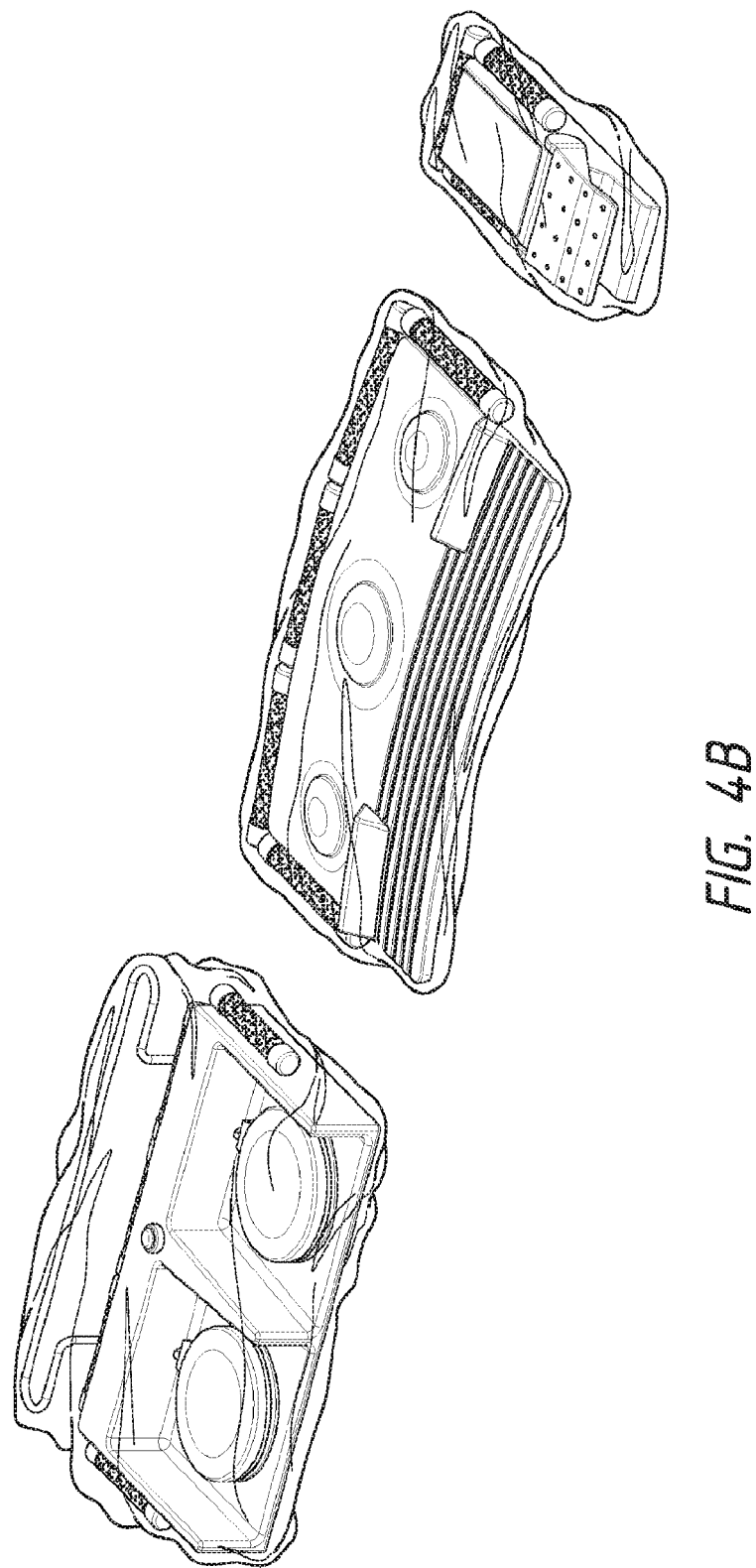

FIGS. 4A-4C illustrate various embodiments of illuminated protective covers on a variety of different-sized devices. As seen, the illuminated protective covers allow each of the devices and their associated foot pedals to be easily identified in a darkened operating room.

Frame

In some examples, the illuminated protective cover can further or alternatively include a frame. The device can be placed within the frame such that the device can be provided with additional protection, for example during a surgical procedure. The frame can also provide sufficient weight to prevent the device and frame from moving during use of the device. In other examples, the frame can provide an additional surface for the attachment of the plurality of illuminating devices. In some examples, the frame can give the device added height such that the top surface of the foot pedal is better illuminated. In some embodiments, the frame can contain the illumination such that the environment around the foot pedal is brightened.

Each of the frames 440, 940 disclosed below can be configured to be part of the device or a separate component. The frames 440, 940 can be reusable or a disposable component that can be discarded after each use. In some examples, the frame can be made of an inexpensive plastic material.

FIGS. 5A-5H illustrate an example of a frame 440. As shown in FIGS. 5A-5H, the frame can include one or more walls, e.g., a top wall, a bottom wall, a left wall, a right wall, and/or a back wall. In some examples, the five (5) walls of the frame 440 form a closed container. In some examples, the top wall, the bottom wall, the left wall, and the right wall form an opening of the frame 440. The frame 440 can provide the illuminated protective cover with additional surfaces to place the illuminating device to better visualize the foot pedal of the device.

Figure 5D:
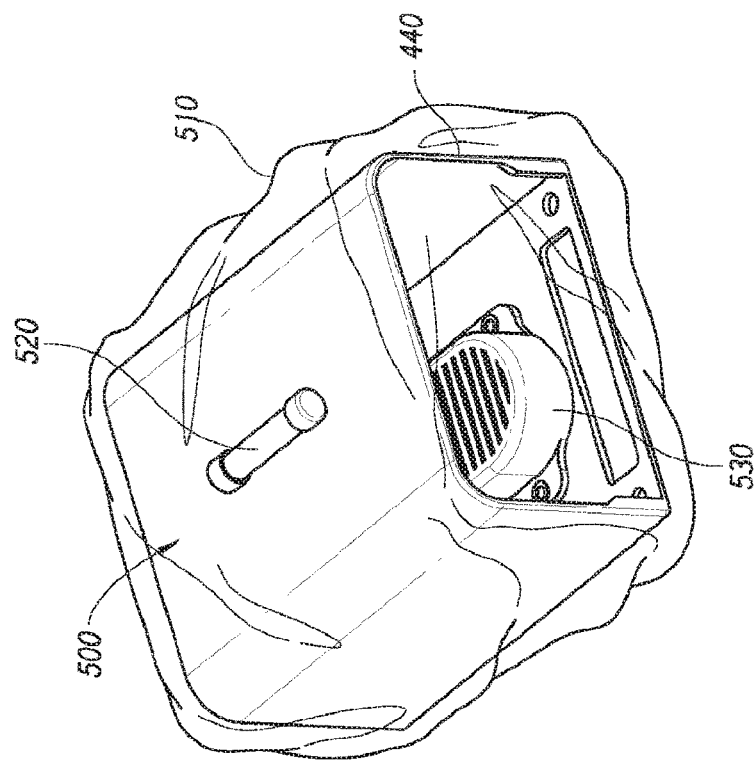
Figure 5C:
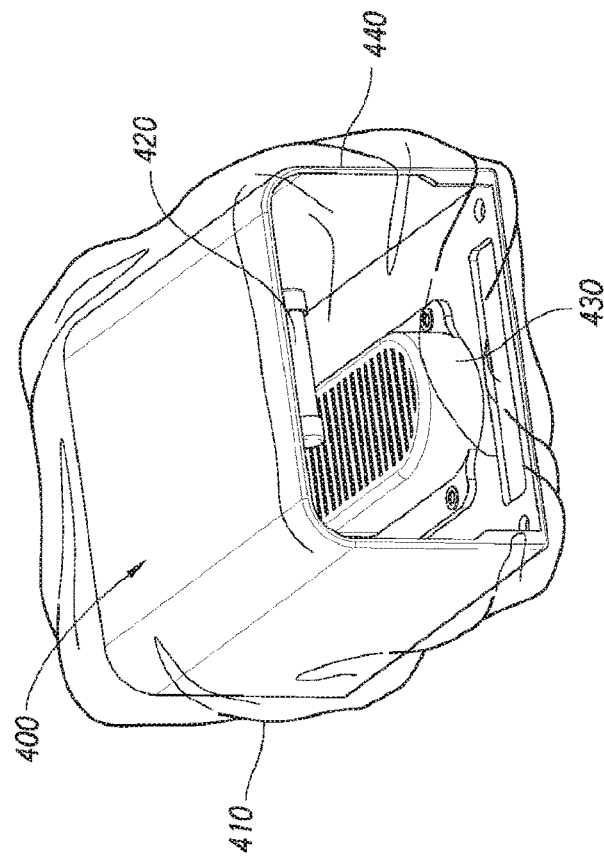

FIGS. 5A-5C illustrate an example of the illuminated protective cover 400 with the frame 440. As illustrated, the frame 440 includes a device 430 placed within the frame 440 such that the device 430 is attached adjacent to the inside bottom surface of the frame 440. The protective sheet 410 of the illuminated protective cover 400 is wrapped around the entirety of the illuminated protective cover 400 to cover the exterior and interior surfaces of the frame 440. As well, the protective sheet 410 seals the device 430 while allowing access to the device 430 by the user by placing his foot through the opening of the frame 440. In the example illustrated in FIGS. 5A-5C, the illuminating device 420 is placed on the interior surface of the top wall. The location of the illuminating device 420 allows for the entirety of the interior of the frame 440 to brighten. In FIGS. 5A-5C, the location of the illuminating device 420 allows the user to identify the foot pedal of the device 430 within the frame 440 while the top surface of the frame 440 prevents the illuminating device 420 from being disruptive to the user in the darkened environment.

FIG. 5D illustrates an example of the illuminated protective cover 500 with the frame 440. The illuminated protective cover 500 resembles or is identical to the illuminated protective cover 400 in many respects. Accordingly, numerals used to identify components of the illuminated protective cover 400 are incremented by a factor of one hundred to identify like features of the system for illuminated protective cover 500. This numbering convention generally applies to the remainder of the figures. Any component or step disclosed in any embodiment in this specification can be used in other embodiments. The illuminating device 520 of the illuminated protective cover 500 is attached to the exterior surface of the top wall of the frame 440. The protective sheet 510 seals the device 530 while allowing access to the device 530 by the user by placing his foot through the opening of the frame 440. The location of the illuminating device 520 allows the user to identify the location of the device 530 placed within the frame 440. The height of the illuminating device 520 can allow the user to position his foot appropriately to access the interior of the frame 440.

FIGS. 5E-5F illustrate the illuminated protective cover 600 with the frame 440. The illuminating device 620 of the illuminated protective cover 600 is located around the entirety of the opening of the frame 440. The protective sheet 610 seals the device 630 while allowing access to the device 630 by the user by placing his foot through the opening of the frame 440. The location of the illuminating device 620 allows the user to locate where his foot should be placed in order to access the device 630 located on the interior of the frame 440.

Figure 5H:
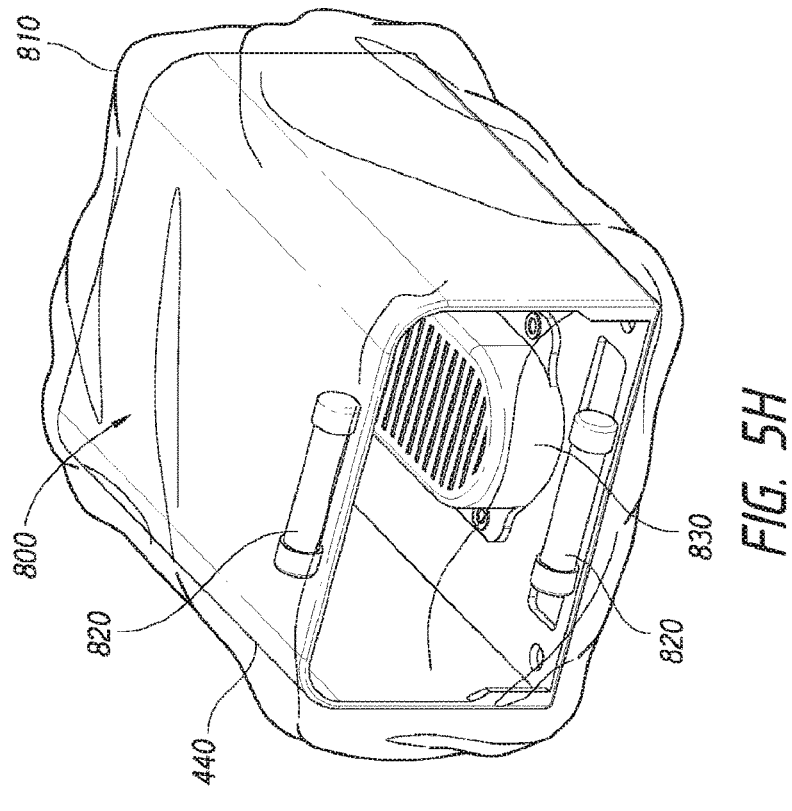
Figure 5G:
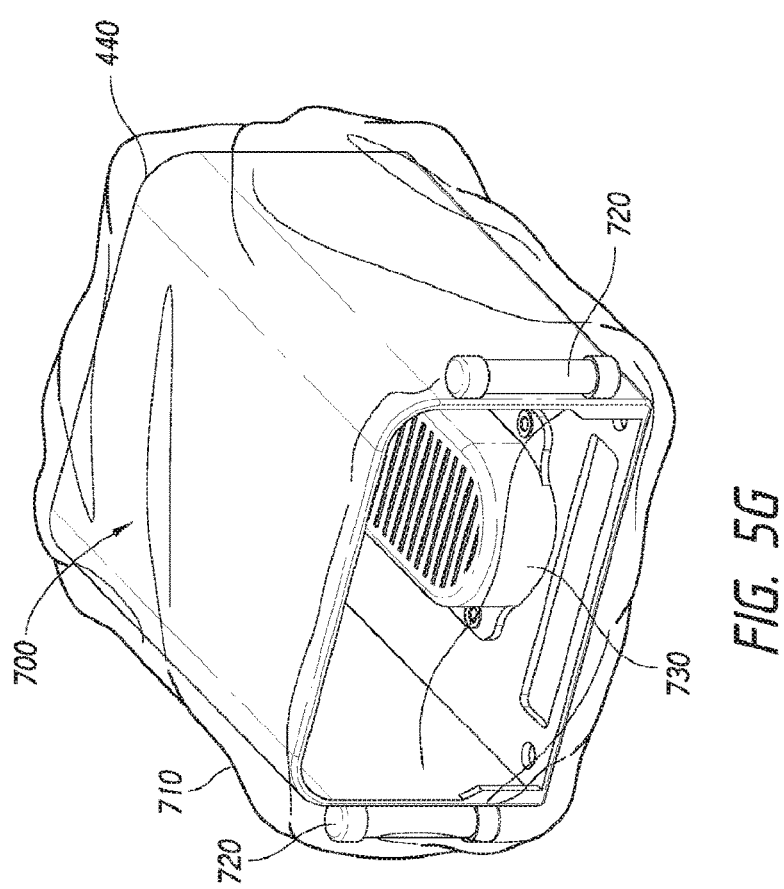
Figure 7:
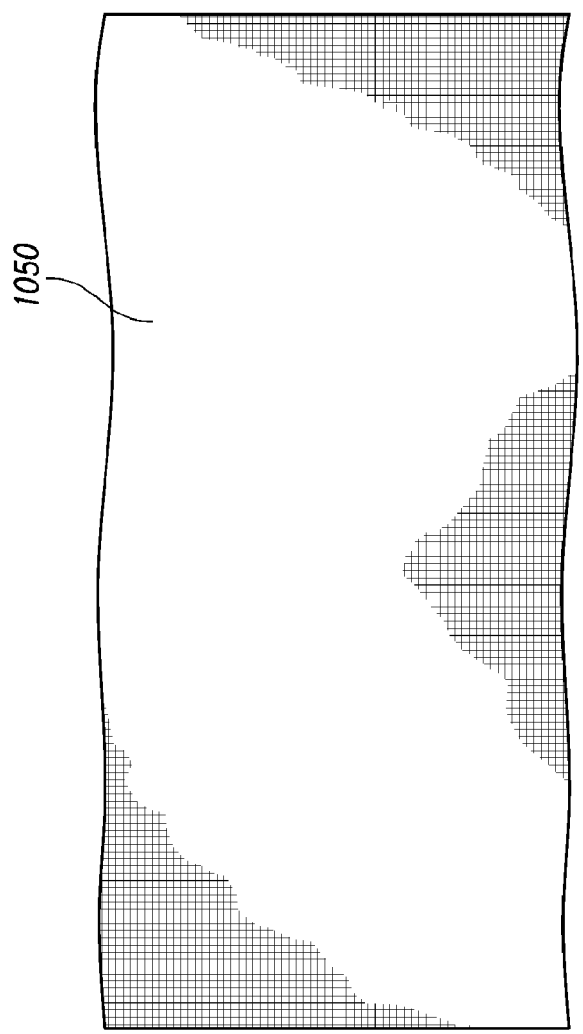
FIG. 7 illustrates an embodiment of an adhesive friction surface.

FIGS. 5G and 5H illustrate illuminated protective covers 700, 800 with a frame 440. In both the illuminated protective cover 700 and illuminated protective cover 800, a pair of illuminating devices 720, 820 are attached to opposing sides of the opening of the frame 440. In the illuminated protective cover 700, the pair of illuminating devices 720 are placed on the left and right sides of the opening of the frame 440. In the illuminated protective cover 800, the illuminating devices 820 are placed on the top and bottom ends of the opening of the frame 440. The protective sheet 710, 810 seals the device 730, 830 while allowing access to the device 730, 830 by the user by placing his foot through the opening of the frame 440. The location of the plurality of illuminating devices 720, 820 provide the user, for example a surgeon, with a reference point as to where the surgeon should place his foot in order to access the surgical device 730, 830 located within the frame 440.

FIGS. 6A-6C illustrate another example of the frame 940. The frame 940 includes a bottom surface 942, a first wall 944, a second wall 946, and a third wall 948. The first wall 944 includes a top edge 944a and a bottom edge 944b. The second wall 946 includes a top edge 946a and a bottom edge 946b. The third wall 948 includes a top edge 948a and a bottom edge 948b. In some examples, a surgical device (e.g. a foot pedal) can be placed adjacent to the bottom surface 942 of the frame 940. Like the frame 440 illustrated in FIGS. 5A-H, the protective cover for the illuminated protective cover can be placed around the frame 940 and the device.

In some examples, the walls (e.g. the first wall 944, the second wall 946, and the third wall 948) of the frame 940 provide an elevated height for the placement of the plurality of illuminating devices 920. In some examples, the plurality of illuminating devices 920 can be secured to the exterior or interior surface of the walls of the frame 940. FIGS. 6A-6C illustrate three combinations of the placement of the illuminating devices 920—but the combinations are not intended to be limiting. The height of each of the plurality of illuminating devices 920 can be varied such to better allow the illumination of the device to be placed within the frame 940. In some examples, the illuminating device 920 can be located near the bottom edge 944b, 946b, 948b of the interior or exterior surface of a wall (e.g. the first wall 944, the second wall 946, the third wall 948) of the frame 940. In some examples, the illuminating device 920 can be located between the top edge 944a, 946a, 948a and bottom edge 944b, 946b, 948b of the interior or exterior surface of a wall (e.g. the first wall 944, the second wall 946, and the third wall 948) of the frame 940. The illuminating device 920 can also be located near the top edge 944a, 946a, 948a of the interior or exterior surface of a wall (e.g. the first wall 944, the second wall 946, and the third wall 948) of the frame 940.

As discussed above, in some examples, each of the illuminating devices 920 can be removably or permanently secured to the frame 940 using adhesive or a separate component (e.g., a wire, a clip, a magnet, or otherwise). In some examples, the frame 940 includes retention components (e.g., one or more projections to hold the illuminating device, an opening or pocket to receive the illuminating device, etc.) that extend from the exterior and/or the interior surface of the first wall 944, the second wall 946, and/or the third wall 948 that the plurality of illuminating devices 920 can be secured to.

Each of the frames 440, 940 disclosed above can be configured to accommodate a device of any size. In some examples, the frames 440, 940 can be adjustable. For example, the top wall, bottom wall, and back wall of the frame 440 can be configured such that the frame 440 can be widened or shortened to accommodate a wider or narrower device. In the same way, the frame 940 may include a bottom surface 942 and a third wall 948 that can be widened or shortened to accommodate a wider or narrower device. The adjustable walls can be constructed of two walls that are mechanically coupled such that they can be configured to slide against each other to lengthen or shorten.

Friction Surface

In some examples, the placement of the illuminated protective cover over the device can cause the bottom of the device to be slippery against the floor. To prevent slippage and/or movement of the device during use, a friction surface 1050 can be attached to (e.g., using an adhesive) or formed into or within a component of the illuminated protective cover. For example, the friction surface 1050 can be placed on the protective cover (e.g., frame or sheet) at the base of the device. The friction surface 1050 can include material properties and/or surface properties (e.g., adhesive properties, texturing) that prevent slippage when placed against the floor or other surface. The friction surface 1050 can reduce slippage such that the illuminated protective covered device remains stationary during use. In some embodiments, the friction surface 1050 can include an adhesive or a rubber surface that prevents slippage when placed against the floor or other surface. In some examples, the friction surface 1050 can be attached to the foot pedal device. In some embodiments, the protective cover can be attached directly to the floor. For example, the protective cover can be attached to the floor using an adhesive.

Methods of Use

Any of the illuminated protective covers described above can be attached to the device in a number of ways. The aforementioned illuminated devices can be attached to the pedal of the device using any of the attachment mechanisms described above. A protective cover can then be positioned over the device and secured in place.

The illuminated devices can also be attached directly to the protective cover. The protective cover, with the attached illuminated devices, can then be positioned over the device.

In some examples, the illuminated devices are first attached to a structure such as a frame. The device is placed within the frame and a protective cover is positioned over and secured about the frame.

In each of the aforementioned examples, the plurality of illuminated devices, the protective cover, and/or the frame may be removable between uses and/or between surgical procedures.

Alternative Configurations

Although not shown, in other embodiments, the illuminating devices can be secured separately from the foot pedal device, the frame, and/or the protective sheet. For example, an illuminating device can be placed under the patient's bed but above the foot pedal of the surgical device such that the illuminating device can illuminate the foot pedal. The illuminating device can be either disposable or reusable. For example, the illuminating device can be battery powered LED lights, chemiluminescent lights (e.g. glow lights, glow sticks) or other types of lights (for example fluorescent, CFL, halogen, PAR, filament, gas discharge, HID) that can be replaced. In this embodiment, the protective sheet is attached around the surface of the surgical foot pedal device. The protective sheet can be transparent or translucent such that the foot pedal is still visible to the surgeon.

Alternatively, the illuminating device(s) can be attached to various structures in the operating room. For example, the illuminating device(s) can be attached to a railing on the side of the operating room table or hung from a cord or cable off of a surface. The illuminating device(s) can be attached to an object using magnets or a plurality of clips. The illuminating device(s) can be attached to a bar and hung down from the side of a table using a bracket. Brackets are frequently readily available in an operating room and the illuminating device(s) can slip into one of these brackets.

The illuminating device(s) (e.g., LED bar) can be placed underneath a table or stand positioned over the foot pedal, with the light from the illuminating device(s) directed downwards to illuminate the area below the table or stand. The illuminating device(s) can line the edges of the underside of the table or stand. The table or stand can have a clear top surface, or have an opened structure. A protective cover can be placed over part or the entirety of foot pedal and/or the lighted table or stand. In other examples, the illuminating device could hang from the side or back of the table or be embedded within it. In some examples, the table for retaining the plurality of illuminating devices can be reusable or disposable.

The illuminating device can be rigid such that it can be configured to extend vertically from the surface of a platform or stand to illuminate a device placed on the platform. The illuminating device can extend any length (e.g. 3-10 inches) from the platform and can be angled in a number of different configurations to provide better visualization of the device, which in some examples can be a surgical device. In some embodiments, an illuminating device can extend vertically from the left and right back corners of a platform and have an additional illuminated device extension connecting the two bars of illuminating devices to provide a frame of illumination. In some configurations, the platform or stand can include a plurality of raised areas on the back and sides of the stand that are configured to hold the device in place.

The placement of the illuminating device can be contained and hidden underneath a divider (e.g. drapes) such that it does not interfere with the user, for example a surgeon operating in low light areas. However, the illuminating device should provide enough light to help adequately visualize the floor in the area right beneath the operating room table where the surgical device and the associated foot pedals would be located.

Study Regarding Use of Illuminated Protective Cover

A study was conducted to determine whether illuminated foot pedals would improve the speed and accuracy of pedal activation during endoscopic procedures. The study was conducted at the Department of Urology at the Loma Linda University Medical Center at Loma Linda Calif., USA.

Introduction/Objectives: Enduorological procedures such as percutaneous nephrostolithotomy (PCNL) commonly involve the use of multiple foot pedals to operate surgical instruments. Their visibility can be obscured in low-light operating room (OR) settings. The purpose of this study is to evaluate the impact of color-coded illumination on speed and accuracy of pedal activation in a simulated intraoperative setting.

Methods:

A simulated PCNL, using a C-arm, laser, and ultrasonic lithotripter (TM) in typical locations in a conventionally lit OR. Foot pedals were placed in three different positions underneath the table in front of the subject. Five attending and five residents/fellows were instructed to activate the instruments by stepping on the foot pedals in a randomized sequence. Pedal position and orientation were randomized for each trial. Time to instrument activation, number of attempted pedal presses, number of missed attempts, and number of wrong pedal presses were recorded. 360 total instrument activations were conducted (18 instruments×10 subjects with and without color-coded pedal illumination). Each subject then completed a survey regarding their experiences and preferences with foot pedal illumination. Data was analyzed using the Mann Whitney U, Wilcoxon signed rank, and chi-square tests with $p<0.05$ indicating statistical significance.

Results:

Use of illuminated pedals was associated with decreased average activation time of all instruments together (6.73±5.18 s vs. 9.19±6.61 s, $p<0.01$) as well as separately (c-arm: 3.53±2.02 s vs. 5.20±3.87 s, $p<0.01$; laser: 13.17±4.14 s vs. 16.63±5.35 s, $p<0.01$: UL: 3.58±1.51 s vs. 5.99±3.62 s, $p<0.01$). Illuminated pedals were associated with a decreased number of total attempted pedal presses (27.5±8.7 vs. 34.5±10.7, $p<0.01$) and missed pedals (2.6±3.2 vs. 8.6±3.7, $p<0.01$). The number of wrong pedals decreased with illumination but this finding did not reach statistical significance (0.1±0.3 vs. 1.3±2.5, $p=0.08$). All subjects reported that illumination made the pedals easier to use and would recommend their use in regular practice ($p<0.01$). 9 of 10 (90%) subjects felt they made fewer mistakes, were more efficient, and felt a greater sense of security with the use of illuminated pedals ($p<0.01$ for each).

Conclusions: Color-coded illumination improved speed and accuracy of pedal activation during enduorological surgery. A questionnaire revealed high surgeons satisfaction, with a greater perception of efficiency, security and efficacy.

Certain Terminology

"Foot pedal" is a broad term that is to be given its ordinary and customary meaning to a person of ordinary skill in the art (i.e., it is not to be limited to a special or customized meaning) and includes, without limitation, any mechanical device (e.g. button, pedal, switch, etc.) that can be engaged to activate a device, which in some embodiments can include a surgical device.

"Sheet" is a broad term that is to be given its ordinary and customary meaning to a person of ordinary skill in the art (i.e., it is not to be limited to a special or customized meaning) and includes, without limitation, any material that can be configured to cover a device and protect the device from moisture and other debris generated during the use of the device, for example to protect a surgical device from moisture and other debris generated during an operation.

"Illuminating device" is a broad term that is to be given its ordinary and customary meaning to a person of ordinary skill in the art (i.e., it is not to be limited to a special or customized meaning) and includes, without limitation, any device that can provide illumination to a surrounding area.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally are not required to conform strictly to the mathematical definitions of the referenced structures, but can encompass structures that are reasonably close approximations.

Conditional language, such as "can," "could," "might," or "may," unless specifically stated otherwise, or otherwise understood within the context as used, is generally intended to convey that certain embodiments include or do not include certain features, elements, and/or steps. Thus, such conditional language is not generally intended to imply that features, elements, and/or steps are in any way required for one or more embodiments.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately," "about," and "substantially" may refer to an amount that is within less than or equal to 10% of the stated amount. The term "generally" as used herein represents a value, amount, or characteristic that predominantly includes or tends toward a particular value, amount, or characteristic.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

For expository purposes, the term "horizontal" as used herein is defined as a plane parallel to the plane or surface of the floor of the area in which the device being described is used or the method being described is performed, regardless of its orientation. The term "floor" can be interchanged with the term "ground." The term "vertical" refers to a direction perpendicular to the horizontal as just defined. Terms such as "above," "below," "bottom," "top," "side," "higher," "lower," "upper," "over," and "under" are defined with respect to the horizontal plane.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

SUMMARY

Although illuminated protective covers have been disclosed in the context of certain embodiments and examples (e.g., foot pedals), this disclosure extends beyond the specifically disclosed embodiments to other alternative embodiments and/or uses of the embodiments and certain modifications and equivalents thereof. For example, any of the disclosed covers can be used on other types of devices, for example any surgical device that is used during a surgical procedure. Various features and aspects of the disclosed embodiments can be combined with or substituted for one another in order to form varying modes of the lighting of the foot pedals. The scope of this disclosure should not be limited by the particular disclosed embodiments described herein.

The methods disclosed herein include certain actions taken by a user; however, they can also include any third-party instruction of those actions, either expressly or by implication. For example, actions such as "attaching at least one illuminating device" include "instructing the attachment of at least one illuminating device."

Any of the covering assemblies described above can be provided as a kit. For example, the kit can include items such as a plurality of illuminating devices, a sheet, and a friction portion. In other examples, the kit can include also include adhesive to attach the plurality of illuminating devices or to secure the sheet.

Certain features that are described in this disclosure in the context of separate implementations can also be implemented in combination in a single implementation. Conversely, various features that are described in the context of a single implementation can also be implemented in multiple implementations separately or in any suitable subcombination. Although features may be described above as acting in certain combinations, one or more features from a claimed combination can, in some cases, be excised from the combination, and the combination may be claimed as any subcombination or variation of any subcombination.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The present application is a Continuation of U.S. Non-Provisional application Ser. No. 15/592,907, titled "ILLUMINATED PROTECTIVE COVERING FOR FOOT PEDALS," filed May 11, 2017, which is a Continuation in Part of International Application No. PCT/US2015/061523, titled "ILLUMINATED PROTECTIVE COVERING," filed Nov. 19, 2015, which claims priority to and the benefit of U.S. Provisional Application No. 62/083,098, titled "FOOT PEDAL LIGHTS," filed Nov. 21, 2014, the full disclosure of which is incorporated herein by reference. This application also claims priority to and the benefit of U.S. Provisional Application No. 62/338,403, titled "ILLUMINATED PROTECTIVE COVERING," filed May 18, 2016, the full disclosure of which is incorporated herein by reference.

In summary, various embodiments and examples of illuminated protective covers have been disclosed. Although the assemblies have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described above, but should be determined only by a fair reading of the claims that follow.

What is claimed is:

1. A system to illuminate one or more foot pedals, the system comprising:
  one or more foot pedals, each of the one or more foot pedals:
    being transitionable from an initial position to a depressed position; and
    having an upper surface and a lower surface, the lower surface being adapted to be positioned on a floor or other surface;
  a plurality of illuminating devices positioned to substantially surround a significant portion of a perimeter of each of the one or more foot pedals to illuminate light therefrom;
  a sheet connected to each of the one or more foot pedals and positioned to substantially cover the upper surface and the lower surface of each of the one or more foot pedals and the plurality of illuminating devices, the sheet being positioned to protect each of the one or more foot pedals from debris, the sheet having an optically transmissive material such that light when illuminating from the plurality of illuminating devices is visible external to the sheet; and
  a friction portion attached to the sheet, the friction portion being positioned on the sheet such that the friction portion is adjacent the bottom surface of each of the one or more foot pedals, the friction portion being positioned to reduce sliding of each of the one or more foot pedals against the floor or other surface.

2. The system of claim 1, further comprising a frame positioned to receive the one or more foot pedal, and wherein the optically transmissive material being sufficiently flexible to substantially conform to a shape of each of the one or more foot pedals.

3. The system of claim 2, the frame having:
  a bottom wall;
  first and second walls extending upward from opposite lateral sides of the bottom wall; and a third wall extending between the first and second walls and along a side of the bottom wall.

4. The system of claim 2, wherein the sheet is further connected to the frame.

5. The system of claim 2, wherein each of the plurality of illuminating devices is positioned on one or more of an inside surface of the frame and an outside surface of the frame.

6. The system of claim 1, further comprising a switch for activating and deactivating the plurality of illuminating devices.

7. The system of claim 1, wherein each of the plurality of illuminating devices is removably attached to one or more of the one or more foot pedal and the sheet.

8. The system of claim 1, wherein each of the plurality of illuminating devices is located at a height above a top surface of each of the one or more foot pedals.

9. An illuminated protective covering to cover and illuminate one or more foot pedals, the covering comprising:
a frame positioned to receive the one or more foot pedals, the frame having a plurality of walls;
a plurality of illuminating devices to illuminate light therefrom, one or more of the plurality of illuminating devices being attached to the plurality of walls of the frame;
a sheet positioned to cover the frame and the plurality of illuminating devices to provide protection from debris, the sheet having:
an optically transmissive material such that light when illuminating from the plurality of illuminating devices is visible external to the sheet; and
a friction portion positioned on the sheet such that the friction portion is adjacent a bottom surface of each of the one or more foot pedals, the friction portion positioned to reduce sliding of the one or more foot pedals against a floor or other surface.

10. The illuminated protective covering of claim 9, wherein the sheet is positioned to connect to the one or more foot pedals, and wherein the optically transmissive material being sufficiently flexible to substantially conform to the one or more foot pedals.

11. The illuminated protective covering of claim 9, wherein each of the plurality of illuminating devices is positioned on one or more of an inside surface of the frame and an outside surface of the frame.

12. The illuminated protective covering of claim 9, wherein each of the plurality of illuminating devices is positioned above the bottom wall of the frame.

13. A method for illuminating one or more foot pedals, the method comprising:
attaching an illuminated covering to the one or more foot pedals, the covering having:
a plurality of illuminating devices, wherein the plurality of illuminating devices surround a significant portion of a perimeter of the one or more foot pedals when attached to the one or more foot pedals; and
a sheet having:
an optically transmissive material such that light when illuminating from the plurality of illuminating devices is visible external to the sheet; and
a friction surface positioned to prevent the one or more foot pedals from slipping against a floor or other surface, the friction surface being adjacent to a lower surface of the one or more foot pedals;
covering upper and lower surfaces of the one or more foot pedals and the plurality of illuminating devices with the sheet, the sheet being positioned to protect the one or more foot pedals from moisture and other debris; and
securing the illuminated covering to the one or more foot pedals.

14. The method of claim 13, further comprising:
attaching the plurality of illuminating devices to a frame, the frame comprising:
a bottom wall;
first and second walls extending upward from opposite lateral sides of the bottom wall; and
a third wall extending between the first and second walls and along a side of the bottom wall;
positioning the one or more foot pedals in the frame such that the first, second, and third walls surround the one or more foot pedals, the one or more foot pedals comprising:
one or more foot pedals, each of the one or more foot pedals being configured to transition from an initial position to a depressed position, and also being positioned to activate a function of the foot pedal when in the depressed position, each of the one or more foot pedals also having an upper surface and a lower surface, the lower surface being adapted to be positioned on a floor or other surface;
wherein the plurality of illuminating devices surround a majority of a perimeter of each of the one or more foot pedals to illuminate light therefrom.

15. The method of claim 14, wherein attaching each of the plurality of illuminating devices to the frame comprises attaching each of the plurality of illuminating devices to one or more of an inner surface of the frame and an outer surface of the frame, and wherein the optically transmissive material being sufficiently flexible to substantially conform to a shape of the one or more foot pedals.

* * * * *